United States Patent [19]

Tusel et al.

[11] 4,405,409

[45] Sep. 20, 1983

[54] METHOD AND APPARATUS FOR DEHYDRATING MIXTURES OF ORGANIC LIQUIDS AND WATER

[76] Inventors: Gunter Tusel, Lieselottenstr. 12, D-6650 Homburg/Saar; Achim Ballweg, Am Hain 4, D-6650 Homburg-Sanddorf, both of Fed. Rep. of Germany

[21] Appl. No.: 308,560

[22] Filed: Oct. 5, 1981

[30] Foreign Application Priority Data

Oct. 6, 1980 [DE] Fed. Rep. of Germany ....... 3037736

[51] Int. Cl.³ .......................... B01D 3/14; B01D 13/00
[52] U.S. Cl. .................................. 202/200; 202/235; 203/19; 203/21; 203/39
[58] Field of Search ............ 210/259, 640, 294, 500.2; 202/200, 235; 203/39, 99, 21, 19; 159/DIG. 27

[56] References Cited

U.S. PATENT DOCUMENTS 2,636,846 4/1953 Loumiet et al. ...................... 203/21
2,981,680 4/1961 Binning ................................. 210/640

*Primary Examiner*—Frank Sever
*Attorney, Agent, or Firm*—Schwartz, Jeffery, Schwaab, Mack, Blumenthal & Koch

[57] ABSTRACT

A method and apparatus for dehydrating mixtures of organic liquids and water comprising consecutive distillation and membrane permeation, wherein at least a portion of the material retained by the separator is passed into indirect heat exchange relationship within the distillation column and recycled to the separator to provide the heat input required for the permeation process.

9 Claims, 1 Drawing Figure

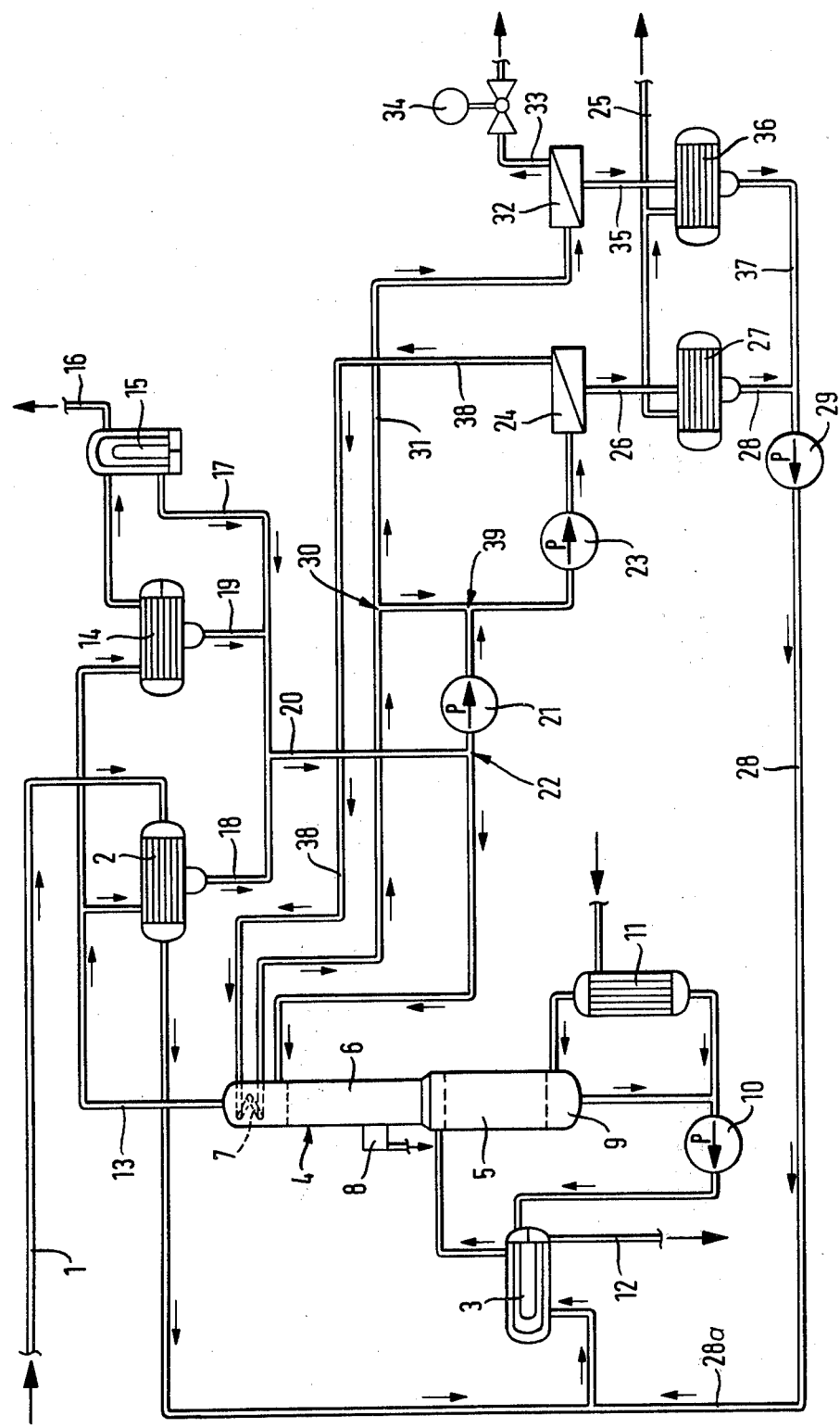

METHOD AND APPARATUS FOR DEHYDRATING MIXTURES OF ORGANIC LIQUIDS AND WATER

FIELD OF THE INVENTION

The invention relates to a method for dehydrating mixtures of organic liquids and water by distillation and permeation, wherein the water content is first reduced by distillation and the remaining dehydration is effected by membrane permeation.

BACKGROUND

Many organic liquids can be mixed with water, in many cases to an unlimited extent. Dehydration purely by distilling requires a large amount of energy. Other problems then arise if the organic liquid forms an azeotropic mixture with water. Some examples of these are ethanol/water, isopropanol/water, ethylacetate/water and pyridine/water. An entrainer is generally used in such cases. The classic example is the use of benzene as an entrainer in dehydrating ethanol. Some of the entrainer is necessarily lost with the exhaust air and waste water. Apart from the resulting costs, the loss of the entrainer puts a strain on the environment. A search has therefore been made for other methods of dehydrating mixtures of organic liquids and water. In principle, the use of membrane permeation for dehydration has been known for a long time; however, no methods which could be used in practice have so far been available.

OBJECTS OF INVENTION

The object of this invention is therefore a viable method of dehydrating aqueous systems by membrane separation.

SUMMARY OF INVENTION

The method of this invention for dehydrating mixtures of organic liquids and water, comprises initially reducing the water content of the mixture by distillation membrane permeation to effect the final dehydration, the improvement being that a quantity of the material retained on membrane permeation is subjected to heat exchange in the same circuit as distillation, that quantity being such that the amount of heat required for membrane permeation of the water is transmitted during heat exchange to the quantity of retained material taken round the circuit.

The invention further concerns an apparatus for dehydrating mixtures of organic liquids and water, comprising a distillation means and a membrane permeation means. It is characterized by a heat exchanger circuit for heat exchange between material retained by the membrane permeation means and the distillate from the distillation means.

The apparatus is preferably characterized by a preheater for preheating the starting mash, a rectifying column with a heat exchanger for heat exchange with the retained material from a membrane module, condensers for condensation of a top stream from the column, pressure pumps and low pressure pumps for creating the pressure difference between the retained material and permeated material side necessary to operate the membrane module and further membrane module, a pressure maintaining means and condensers for condensing the permeated material from the membrane modules.

DETAILED DESCRIPTION AND PREFERRED EMBODIMENTS

The method of the invention is particularly suitable for dehydrating organic liquids which form an azeotropic mixture with water and are therefore especially difficult to separate by distillation. From the point of view of energy costing the dehydration of ethanol should be mentioned in particular. The method of the invention is considerably cheaper than conventional processes. In addition it avoids the use of entrainers with the resultant damage to the environment.

The membranes that are used in practice in the method of the invention are so-called membrane modules. They are preferably plate or nest of tube modules so that, given the small effective pressure difference between the retained and permeated material, short current paths can be obtained and thus only a slight drop in pressure for the flow of permeate. The membranes themselves may be e.g. modified cellulose acetate membranes, as described in Chemie-Technik 8 (1979) 611 to 617 for the separation of isopropanol/water.

In a preferred embodiment the volume of the retained material circuit is chosen so that the temperature at which the retained material leaves the membrane or membrane module is well above the temperature of the cooling water. With normal cooling water temperatures at 15° to 30° C., this means that the discharge temperature for the retained material must be well above this, e.g. at 50° C.

In another preferred embodiment, membrane permeation is carried out in two stages, a membrane with lower selectivity being used in the first stage and one with higher selectivity in the second. The membranes with relatively low selectivity are preferably cellulose triacetate membranes with a short saponification time, so that the majority of the water can be separated as quickly as possible, with a high permeation speed. The membranes with higher selectivity are preferably made of cellulose triacetate with a longer saponification time, since in this case only a small amount of water has to be separated. This compensates for the fact that the higher selectivity of the membrane achieved by the longer saponification time reduces the speed of permeation. Details of the dependence of permeation speed on saponification time can be found in Chemie-Technik, loc. cit.

When membrane permeation takes place in two stages it is preferable that only retained material from the first membrane stage should be included in the retained material heat exchange circuit with the distillation stage, in order to avoid additional expenditure on a second heat exchange circuit.

It is preferable for the water content of the mixture being fed into the second permeation stage to be chosen—depending how anhydrous the final product has to be—so that its heat capacity is sufficient for permeation of the remaining water. For this purpose it is further preferable to ensure that the temperature at which the retained material leaves the second membrane stage is well above that of the cooling water.

In another preferred embodiment the method of the invention is applied to dehydration of ethanol, starting with normal agricultural mash, by dehydrating the mash to approximately 80% by weight ethanol in the distillation stage, bringing the ethanol content to approximately 95% by weight in the first membrane stage, and making it virtually anhydrous in the second membrane stage.

The invention will now be described with reference to the accompanying drawing. This shows a preferred apparatus for carrying out the method of the invention, using two-stage membrane separation.

The starting material in the drawing is ordinary ethanol mash with an ethanol content of 8.8% by weight. The mash is fed in through a pipe 1, passes through a product condenser 2 and preheater 3, then enters a separating portion 5 of a rectifying column 4. The column also contains a reinforcing portion 6 and a heat exchanger 7. Higher boiling components, chiefly fusel oils, can be discharged as a side stream at 8.

The ethanol mash is heated to boiling temperature in the preheater 3. The heat source is the distiller's wash in the sump 9 of the column 4. This is fed into the preheater 3 by means of a pump 10 and discharged through a pipe 12. Energy is supplied to the column 4 by means of a vapour heated circulation evaporator 11.

A product stream with an 80% by weight ethanol content is drawn off from the rectifying column 4 through a pipe 13, as the top stream. Condensation takes place in the product condenser 2 and, depending on the capacity of this condenser, the rest of the condensation takes place in a further condenser 14. More volatile components are condensed in a final condenser 15. Uncondensed gases and vapours are discharged through a pipe 16; the condensate left in the condenser 15 passes through a pipe 17 and is combined with the product streams which emerge from the condensers 2 and 14 through pipes 18 and 19. The total flow is fed through a pipe 20 to a membrane module 24 by means of a pump 21 and a pump 23. The necessary return flow for the column 4 is picked up at 22.

The membrane used in the membrane module 24 allows for rapid separation of water at a high-permeation speed. Only relatively slight demands are made of its selectivity.

At the 'retained material' side the membrane module 24 is operated at a pressure of approximately 3 bars, generated by the pumps 21 and 23. At the permeat side a pressure of approximately 70 mbar is maintained by means of a vacuum pump (not shown) through a pipe 25. The permeat consists substantially of water containing up to 10% by weight of ethanol. It is fed through a pipe 26 into a condenser 27, and after condensation is returned to the process through pipes 28, 28a and a pump 29.

At 30 a part-stream of product is diverted through a pipe 21 and fed to a further membrane module 32. A membrane of higher selectivity is used in the module 32, so that the required purity of the product is obtained.

Anhydrous ethanol (ethanol content 99.8% by weight) is discharged through a pipe 33 and a pressure maintaining valve 34. The permeate left in the membrane module 32 substantially consists of water, containing up to 10% by weight of ethanol. It is fed through a pipe 35 into a condenser 36 and, after condensation, is returned to the process through a pipe 37.

A circuit stream is taken from the membrane module 24, via a pipe 38, the heat exchanger 7 and the pump 23; the top stream from the column is fed in at 39 and a part stream of product drawn off at 30. In the quantity balance the sum of part stream of product drawn off at 30 plus permeat discharged through the pipe 26 is equal to the top stream from the column fed in at 39.

95% ethanol is obtained from the membrane module 24 on the 'retained material' side. Of this a part stream is drawn off at 30 and fed into the second membrane module 32, from which it emerges with an ethanol content of 99.8% by weight. On the basis of the conditions used, which can be seen in the following table, the stream taken through the circuit membrane module 24-pipe 38-heat exchanger 7-pump 23-membrane module 24, of 8122 kg/h, is considerably larger than the top stream from the column which is fed into the circuit at 39 (1421 kg/h). On the basis of the water separated in the membrane module 24 (251 kg/h), the quantity of product diverted from the circuit at 30 (95% by weight ethanol content) is only 1170 kg/h.

The procedure described provides two important advantages. Firstly the intake concentration for the membrane module 24 is increased from 80% by weight ethanol in the top stream from the column to 92.5% by weight (after mixing with the circuit stream). Secondly, the circuit arrangement enables the condensation heat, which would otherwise be lost with the cooling water, to be utilised in operating the rectifying column 4. Furthermore it is possible to work with a lower reflux ratio of only approximately 2 in the rectifying column, as compared with 3.5 to 4 in conventional processes.

As a result of these advantages the method of the invention can be carried out with considerable energy saving as compared with conventional processes. The energy balance shows that, as compared with conventional processes which require a steam consumption of approximately 5 kg/l alcohol, the energy requirement with the method of the invention, converted to steam consumption, is only 1.6 kg steam/l alcohol. In other words, the energy requirement for the method of the invention is only ⅓ of the energy requirement for known processes.

TABLE

| Description | Place* | Quantity kg/hr | % by weight ethanol | Temperature °C. |
|---|---|---|---|---|
| Mash | 1 | 12720 | 8.8 | |
| Top product | 13 | 4262 | 80 | 78 |
| Retained discharge from first membrane module | 38 | 8122 | 95 | 50 |
| Heat exchanger | 7 | 8122 | 95 | 72 |
| Recycle circuit | 30–39 | 6952 | 95 | 72 |
| Top product feed to first membrane module | at 39 | 1421 | 80 | 78 |
| Intake into first membrane module | 24 | 8373 | 92.5 | 73.6 |
| Intake into second membrane module | 31 | 1170 | 95 | 72 |
| Condensed water | 28 | 251 | up to 10 | |
| Condensed water | 37 | 67 | up to 10 | |
| Product ethanol | 33 | 1103 | 99.8 | |

*Reference numerals refer to accompanying drawing.

We claim:

1. In a method of dehydrating a mixture of an organic liquid and water, which comprises subjecting the mixture to initial distillation to remove an initial quantity of water followed by membrane permeation to remove substantially the remaining water, the improvement which comprises withdrawing at least a portion of the material retained by the membrane separator, passing that material into indirect heat exchange relationship within the distillation column and recycling at least a portion of that withdrawn material back to the separator, the quantity of such recycle stream being such that substantially the whole of the heat required for the membrane permeation is transmitted to the recycle stream during said heat exchange within the distillation column.

2. The method of claim 1, wherein the volume of the recycle stream is large enough to make the temperature at which the retained material leaves membrane permeation well above the temperature of the cooling water.

3. The method of claim 1, wherein the membrane permeation is carried out in two stages, with a membrane of lower selectivity being used in the first stage and one with higher selectivity in the second.

4. The method of claim 3, wherein the recycle stream of retained material is drawn solely from the first membrane stage.

5. The method of claim 4, wherein the withdrawn stream of retained material from the first separator, after passing through said heat exchange within the distillation column is split with one part being recycled to the first separator and the remainder being passed to the second membrane separator.

6. The method of claim 5, wherein the water content of the mixture fed to the second membrane stage is chosen so that the heat capacity of the mixture is sufficient for permeation of the remaining water.

7. The method of claim 3, as applied to the dehydration of an aqueous ethanol mash wherein the mash is dehydrated to approximately 80% by weight ethanol in the distillation stage, and that the ethanol content is brought to approximately 95% by weight in the first membrane stage and made virtually anhydrous in the second.

8. Apparatus for dehydrating mixtures of an organic liquid and water comprising a distillation column and a membrane separator connected in series for the initial distillation and subsequent membrane separation of the mixture to remove water remaining in the distillate from the distillation column and including a recycle circuit for withdrawing at least a portion of the material retained by the separator, a heat exchanger within the distillation column connected in said recycle circuit for indirect heat exchange between said portion of withdrawn material, and a recycle conduit for return of at least a portion of the heated withdrawn material from the heat exchanger to the membrane separator.

9. Apparatus according to claim 8 including two membrane separators, wherein said recycle circuit connects the first separator to the heat exchanger for the feeding therethrough of the whole of the material retained by the first separator, and the recycle conduit connects with both the first and second separators for recycling a part of the heated retained material to the first separator and the remainder to the second separator.

* * * * *